United States Patent [19]

Baumgardner et al.

[11] Patent Number: 5,186,843
[45] Date of Patent: Feb. 16, 1993

[54] BLOOD SEPARATION MEDIA AND METHOD FOR SEPARATING PLASMA FROM WHOLE BLOOD

[75] Inventors: John S. Baumgardner, Aspers; Mark D. Loewen, Carlisle, both of Pa.

[73] Assignee: Ahlstrom Filtration, Inc., Chattanooga, Tenn.

[21] Appl. No.: 733,592

[22] Filed: Jul. 22, 1991

[51] Int. Cl.$^5$ .................. B01D 37/00; B01D 39/00
[52] U.S. Cl. .................. 210/767; 210/505; 210/507; 210/508; 210/509; 422/101; 436/177
[58] Field of Search .................. 210/500.29, 500.38, 210/503, 505, 507, 508, 509, 767, 782, 929, 500.26, 496; 422/101; 436/177; 428/373, 903

[56] References Cited

U.S. PATENT DOCUMENTS

| | | |
|---|---|---|
| 3,036,894 | 5/1962 | Forestiere . |
| 3,092,465 | 6/1963 | Adams et al. . |
| 3,260,413 | 7/1966 | Natelson .................. 222/144 |
| 3,448,041 | 6/1969 | Swank . |
| 3,552,925 | 1/1971 | Fetter . |
| 3,552,928 | 1/1971 | Fetter . |
| 3,579,303 | 5/1971 | Pickering . |
| 3,630,957 | 12/1971 | Rey et al. .................. 252/408.1 |
| 3,663,374 | 5/1972 | Moyer et al. . |
| 3,791,933 | 2/1974 | Moyer et al. . |
| 3,937,860 | 2/1976 | Gusman et al. .................. 428/234 |
| 3,983,005 | 9/1976 | Goodhue et al. . |
| 4,012,325 | 3/1977 | Columbus .................. 210/516 |
| 4,069,017 | 1/1978 | Wu et al. . |
| 4,092,246 | 5/1978 | Kummer .................. 210/504 |
| 4,132,650 | 1/1979 | Kirsch et al. .................. 210/505 |
| 4,144,306 | 3/1979 | Figueras .................. 422/56 |
| 4,157,967 | 6/1979 | Meyst et al. .................. 210/449 |
| 4,188,197 | 2/1980 | Amberkar et al. .................. 55/382 |
| 4,189,382 | 2/1980 | Zine .................. 210/516 |
| 4,223,089 | 9/1980 | Rothe et al. .................. 435/12 |
| 4,234,317 | 11/1980 | Lucas et al. . |
| 4,239,516 | 12/1980 | Klein .................. 55/389 |
| 4,246,107 | 1/1981 | Takenaka et al. .................. 210/806 |
| 4,256,693 | 3/1981 | Kondo et al. .................. 422/56 |
| 4,292,272 | 9/1981 | Kitajima et al. .................. 422/57 |
| 4,293,378 | 10/1981 | Klein .................. 162/145 |
| 4,312,834 | 1/1982 | Vogel et al. .................. 422/56 |
| 4,330,410 | 5/1982 | Takenaka et al. .................. 210/767 |
| 4,477,575 | 10/1984 | Vogel et al. .................. 210/509 |
| 4,505,823 | 3/1985 | Klein .................. 210/668 |
| 4,687,697 | 8/1987 | Cambo et al. .................. 428/201 |
| 4,701,267 | 10/1987 | Watanabe et al. .................. 210/505 |
| 4,734,208 | 3/1988 | Pall et al. .................. 210/767 |
| 4,743,371 | 5/1988 | Servas et al. .................. 210/188 |
| 4,753,776 | 6/1988 | Hillman et al. .................. 210/505 |
| 4,765,915 | 8/1988 | Diehl .................. 210/505 |
| 4,786,603 | 11/1988 | Wielinger et al. .................. 436/69 |
| 4,810,394 | 3/1989 | Masuda .................. 210/505 |
| 4,816,224 | 3/1989 | Vogel et al. .................. 210/505 |
| 4,925,560 | 5/1990 | Sorrick .................. 210/387 |
| 4,981,591 | 1/1991 | Oestreicher .................. 210/502.1 |

FOREIGN PATENT DOCUMENTS 0313348 4/1989 European Pat. Off. .
2018151 10/1979 United Kingdom .

OTHER PUBLICATIONS

Averso, *American Laboratory*, vol. 5, No. 4, (Apr. 1976), pp. 97, 98, 101, 102, 104.

*Primary Examiner*—Robert A. Dawson
*Assistant Examiner*—Sun Uk Kim
*Attorney, Agent, or Firm*—Small Larkin Kidde & Golant

[57] ABSTRACT

A single-layer blood separation medium for separating erythrocytes from whole blood and made of a composite including glass microfibers, cellulose fibers, and synthetic textile fibers, having enhanced tensile strength and lower absorptive capacity compared to binderless glass microfiber sheet. The mean bulk density of the glass microfiber component is less than 0.1 g/cm$^3$, and is typicaly about 0.05 g/cm$^3$.

20 Claims, No Drawings

BLOOD SEPARATION MEDIA AND METHOD FOR SEPARATING PLASMA FROM WHOLE BLOOD

BACKGROUND OF THE INVENTION

1. Field of the Invention

This invention relates to media for separating plasma or serum from whole blood.

Medical diagnostic assays are routinely performed on blood samples to determine the clinical status of patients by chemically detecting the presence and concentration of dissolved blood components, commonly referred to as analytes. Many of these assays are performed on a solid support such as a membrane or fibrous medium, with a color change occurring in relation to the concentration of the analyte being assayed. This color is then read visually or photometrically.

When using whole blood, the colored constituents of blood, viz, the erythrocytes, commonly known as red blood cells, can interfere with interpretation of the assay. For this reason, and as is well-known, the erythrocytes must be removed from the whole blood prior to the assay being performed on the remaining fluid. One known way of separating erythrocytes from plasma or serum is through centrifugation. However, this procedure entails an added, time-consuming step which is incompatible with situations requiring rapid diagnosis. In such cases the physician requires a system where a small amount of blood drawn from the patient can be assayed without having to centrifuge the sample. Specifically, it is desirable that erythrocytes can be quickly separated from blood such as is drawn from a fingerstick, thus leaving the lightly colored plasma to be available for subsequent assay.

In addition to separating erythrocytes from whole blood, the separation process must not cause hemolysis, i.e., rupture, of the erythrocytes during separation; otherwise, erythrocyte fragments could interfere with accurate measurement. Also, the components of the plasma or serum, such as proteins and lipids, must not be denatured by, nor undergo binding with, the separation medium. Finally, the separated fluid must be transported beyond the point of separation so that a sufficient quantity will be available for subsequent assay.

2. Description of the Prior Art

Several approaches to the problem of performing rapid diagnostic assays other than centrifugation have been developed. In one approach, such as is disclosed in U.S. Pat. No. 4,256,693 to Kondo et al. and U.S. Pat. No. 4,810,394 to Masuda, whole blood is allowed to migrate through successive layers of different materials where each layer performs separate and distinct functions. In another approach, as disclosed in U.S. Pat. Nos. 4,477,575 and 4,816,224 to Vogel et al., a separation layer consisting of glass microfibers having a bulk density of 0.1 to 0.5 g/cm$^3$ has been used to separate erythrocytes from whole blood.

There are several known problems associated with these two approaches. First, manufacturing of multi-layer separation media is expensive and difficult in comparison to manufacture of single-layer media which can perform the same or equivalent diagnostic functions. Secondly, papers or packings consisting entirely of glass microfibers are inherently weak and require great care in handling relative to multilayer media, membranes and other fibrous media typically used in diagnostic procedures. This characteristic, often referred to as fragility, is particularly serious in high volume diagnostic facilities where automated handling of materials is required. Although it is known that the strength of glass microfiber papers can be increased by adding binders which traditionally have been latex-based binders, such as polyvinyl acetate (PVA) or acrylics, these materials, or substances associated with their use, such as surfactants, are known to cause chemical interference with assays of the type contemplated in the present invention. Moreover, no specific composite media including such materials are known which can separate erythrocytes from whole blood without causing chemical interference.

OBJECTS OF THE INVENTION

An object of the present invention is to provide single-layer media for separating erythrocytes from whole blood, and which have improved strength characteristics compared to binderless glass microfiber media.

A further object of the invention is to provide single-layer, composite blood separation media which do not cause erythrocytes to undergo hemolysis during the separation process.

A still further object of the invention is to provide single-layer, composite blood separation media which will not denature or bind with the components of the plasma or serum.

A still further object of the invention is to provide single-layer, composite blood separation media which effectively transport the separated plasma or serum from the separation region.

SUMMARY OF THE INVENTION

The present invention is a blend of several different types of fibers formed into a single-layer, composite fibrous sheet using conventional paper-making technology.

The individual fiber types do not form distinct layers, but rather are intermixed in a randomly dispersed fibrous matrix. The medium includes a blend of glass microfiber, cellulose fiber, and synthetic staple fiber. Optionally, synthetic binder fiber may be added to the blend to provide increased tensile strength. The media of the present invention are manufactured in varying thicknesses, typically about 0.175 to 0.650 mm, and have a typical bulk density of about 0.25 g/cm$^3$.

The cellulose fibers are derived from plant matter including wood fiber, cotton fiber, cellulosic derivatives such as rayon and cellulose acetate, or other commercially available fibers such as are generally used in paper making.

The glass microfiber component consists of alkali-containing or alkali-free borosilicate glass or pure quartz fibers, having a mean fiber diameter of 0.3 to 0.7 $\mu$m. The bulk density of the glass microfiber component is less than 0.1 g/cm$^3$, and is typically about 0.05 g/cm$^3$. Other technical glass fibers having a mean diameter in this range are believed to be suitable.

The synthetic staple fibers include polyester, polypropylene, polyethylene or other commercially available synthetic textile fibers which have melting temperatures higher than the melting temperatures of the synthetic fibers used in the binder fiber component.

The synthetic binder fibers include polyester, polypropylene, polyethylene or other commercially available synthetic textile fibers which soften and melt at temperatures which are low relative to the melting point temperatures of the synthetic staple fibers.

The present invention and other objects, aspects and advantages thereof will be apparent from considering the following description of the preferred embodiments.

DESCRIPTION OF THE PREFERRED EMBODIMENTS

While the present invention is susceptible of various modifications and alternative constructions, it is to be understood that it is not intended to limit the invention to the particular forms disclosed. On the contrary, the present invention is intended to cover and apply to all modifications, equivalents and alternative constructions following within the spirit and scope of the invention as expressed in the appended claims.

A. THREE-COMPONENT MEDIA

A first preferred embodiment of the present invention is a fibrous single-layer, composite sheet including three types of fibers randomly intermixed: glass microfibers; cellulose fibers; and synthetic staple fibers.

The composite sheet is manufactured using a wet-laid paper-making process comprising multiple, sequential steps such as is described in E. C. Libby, ed., *Pulp and Paper Science and Technology*, Vol. II, New York, McGraw-Hill 1962, and G. A. Smook, *Handbook for Pulp and Paper Technologies*.

Specifically, in step 1, predetermined amounts of selected fibers and water are placed in a pulper or beater, where the fibers are mixed and dispersed evenly in the water to form a slurry. Some mechanical work can also be performed on the fibers to affect physical parameters such as permeability, surface properties, and fiber structure. In step 2, the slurry is moved to a mixing chest where additional water is added and the fibers are homogeneously blended. In step 3, the slurry is moved to a machine chest where one or more pulper or beater charges can be combined, allowing for a transfer from a batch to a continuous process. Slurry consistency is defined and maintained; agitation is maintained to assure even dispersion of fibers. In an optional step 4, fibers can be run through a refiner to adjust physical parameters. In step 5, the slurry is pumped onto a moving wire screen where water is removed by means of gravity and suction. As water is removed, the fibers form into a paper mat having characteristics determined by the slurry flow rate, machine speed, and drainage parameters. In an optional step 6, the sheet can be pressed slightly to compact the paper or modify its surface characteristics. In step 7, the paper mat moves through a drying section consisting of heated cans where most of the remaining water is removed. Heat is also applied to melt the binder fibers, resulting in fiber-to-fiber bonding for improved strength. In step 8, the finished paper media are taken up by a reel.

The glass microfiber component includes alkali-containing or alkali-free borosilicate glass or pure quartz fibers having a mean diameter in the range 0.3 to 0.7 $\mu$m.

The cellulose fiber component consists of plant matter such as wood fiber and/or cotton fiber, cellulose derivatives such as rayon and/or cellulose acetate, and/or other commerically available fibers generally used in paper-making. Cotton linter fiber is preferred over wood pulp fiber because it yields slightly better separation quality and is perceived as a cleaner product for clinical diagnostic use.

The synthetic staple component consists of polyester fiber (PET), polypropylene fiber (PP), polyethylene fiber (PE) and/or other commercially available synthetic textile fibers which have melting point temperatures sufficiently high to be structurally unaffected when the paper mat, i.e., the fibrous sheet, is passed through the heated cans in step 7 of the paper-making process. The melting point temperature of polyester fibers, polypropylene fibers, and polyethylene fibers is about 475° F., 320° F., and 230° F., respectively. PET is preferred since it better withstands the highest drying temperatures used in the paper-making process. PET with 1.5 denier and 0.25 inch length fibers is preferred relative to PET with other deniers and fiber lengths.

When a small amount of blood is applied to the top surface of the fibrous sheet, the blood sample spreads radially from the point of application. The glass and cellulose fibers are hydrophilic and serve to wick the plasma or serum along the sheet's surface as well as into its interior, while the erythrocytes are trapped near the point of application in inter-fiber interstices which typically are smaller than the erythrocyte size. Alternatively, when one end of the fibrous sheet is brought into contact with the surface of a sample of whole blood, the sheet acts to wick a small quantity of blood. The plasma or serum is wicked a greater distance along the sheet than are the erythrocytes, thereby effecting separation.

Experiment has shown that the erythrocytes do not undergo hemolysis during this separation process, and that the separation process does not cause the components of the plasma or serum, such as proteins and lipids, to denature or to bind with any of the materials in the fibrous composite.

Table 1 shows the typical percentages of components used in a first series of tests which demonstrated that separation does not occur when glass microfibers are omitted from the fiber mixture.

TABLE 1

| Media Exhibit No Separation when Glass Microfiber is Absent | | | | |
|---|---|---|---|---|
| Run No. | Cellulose (%) | Glass (%) | Synthetic Staple (%) | Separation Quality |
| 1 | 45 | 0 | 55 | None |
| 2 | 25 | 0 | 75 | None |

Several series of tests were conducted using a variety of three-component compositions to assess the separation quality of the resultant single-layer media as evidenced by uniformity of separation, width of the separation zone, absorption time of the whole blood, and minimal hemolysis of erythrocytes.

Table 2 shows the results of varying the mean diameter of the glass microfibers while fixing the percentages at 20% for the glass microfibers, 25% for cellulose, and 55% for the synthetic staple fibers. These tests show that separation occurs when using glass fiber having mean diameters of 0.32–0.65 $\mu$m. No separation occurred when the glass microfibers had a mean diameter of 1.0 $\mu$m.

TABLE 2

| Separation Occurs when Using Glass Microfiber of 0.32–0.65 $\mu$m Mean Diameter | | | | |
|---|---|---|---|---|
| | | Glass | | Synthetic Staple |
| Run No. | Cellulose (%) | Mean Diam. ($\mu$m) | % | (PET) (%) | Separation Quality |
| 3 | 25 | 0.32 | 20 | 55 | Poor |
| 4 | 25 | 0.40 | 20 | 55 | Fair |

TABLE 2-continued

Separation Occurs when Using Glass Microfiber of 0.32–0.65 μm Mean Diameter

| Run No. | Cellulose (%) | Glass Mean Diam. (μm) | % | Synthetic Staple (PET) (%) | Separation Quality |
|---|---|---|---|---|---|
| 5 | 25 | 0.50 | 20 | 55 | Fair |
| 6 | 25 | 0.65 | 20 | 55 | Poor |
| 7 | 25 | 1.0 | 20 | 55 | None |

Table 3 shows the effect of varying the percentages of glass microfiber and synthetic staple fiber while maintaining the percentage of cellulose at 25%. Best separation occurred using glass microfiber of mean diameter 0.40 μm. These results demonstrate that the optimum separation occurs with a glass microfiber content of 20 percent.

TABLE 3

Varying the Percentage of 0.40 μm Glass Microfiber Results in "Fair" Separation Quality at a Level of 20% Glass Fiber by Weight

| Run No. | Cellulose (%) | Glass (%) | Synthetic Staple (PET) (%) | Separation Quality |
|---|---|---|---|---|
| 4 | 25 | 20 | 55 | Fair |
| 8 | 25 | 30 | 45 | Poor |
| 9 | 25 | 40 | 35 | Poor |

Table 4 shows that good separation quality is achieved when the percentage of cellulose fiber is in the range 30–40 percent, the percentage of glass microfibers having 0.40 μm mean diameter is 20 percent, and the percentage of PET synthetic staple fiber is in the range 40–50 percent.

TABLE 4

Good Separation Quality For Three-Component Media Occurs with 30–40% Cellulose, 20% 0.40 μm Glass, and 40–50% PET

| Run No. | Cellulose (%) | Glass (%) | Synthetic Staple (PET) (%) | Separation Quality |
|---|---|---|---|---|
| 10 | 30 | 20 | 50 | Good |
| 11 | 40 | 20 | 40 | Good |
| 12 | 20 | 20 | 60 | Poor |
| 13 | 50 | 30 | 20 | Fair |

Based on the foregoing results, it is concluded that experiment has shown that separation of erythrocytes from whole blood is effected in three-component, single-layer, composite media of the present invention when the following percentages by weight of the individual constituents are used: glass microfiber, 20–40%; cellulose, 20–50%; and synthetic staple fiber, 20–60%. The individual percentages are such that the total percentage is 100%.

Optimum separation as determined by uniformity of the separation, width of the separation zone, absorption time of the whole blood, and minimal hemolysis of erythrocytes, occurs when the mean diameter of the glass microfibers is 0.4 μm and the percentages by weight of the individual constituents are: glass microfiber, 20%; cellulose, 35%; and PET synthetic staple fiber, 45%. This percentage of glass microfiber results in a bulk density of less than 0.1 g/cm$^3$ of glass microfiber material, typically about 0.05 g/cm$^3$.

B. Four-Component Media

A second preferred embodiment of the present invention is a fibrous single-layer, composite sheet having four types of fibers randomly intermixed: glass microfibers; cellulose fibers; synthetic staple fibers; and synthetic binder fibers.

Materials used for the glass microfibers, cellulose fibers, and synthetic staple fibers are as in the first preferred embodiment. The synthetic binder fibers consist of polyester, polypropylene, polyethylene and/or other polymers commercially available as synthetic textile fibers. The binding fibers have a melting point which is low relative to the melting point of the staple fibers, so that application of heat in step 7 of the paper-making process functions to melt the binding fibers while not melting the staple fibers, thereby binding together the fibers. Inclusion of binder fibers functions to increase tensile strength thereby facilitating handling. The medium maintains its hydrophillicty such that no surfactants need be added which could possibly interfere with desired reactions. Polyester binder fiber (PBF) is preferred because it is the corresponding binder fiber to the preferred PET staple fiber.

Table 5 shows the separation quality for various combinations of a four-component mixture, including cellulose fibers, 0.4 μm glass microfibers, PET staple fibers, and up to 10 percent PBF binder fibers. These results demonstrate that to achieve at least "fair" separation, glass microfiber of 0.40 μm needs to be present at 20 percent. Best separation quality results with levels of 50 percent cellulose, 20 percent glass microfibers, 20 percent PET staple fibers, and 10 percent PBF binder fibers.

Table 6 shows that when the PBF binder fiber content is varied, optimum separation occurs for a PBF binder fiber level of 10 percent.

TABLE 5

"Excellent" Separation Quality For Four-Component Media Was Seen With Run 14

| Run No. | Cellulose (%) | Glass (%) | Synthetic Staple (PET) (%) | Synthetic Binder (PBF) (%) | Separation Quality |
|---|---|---|---|---|---|
| 14 | 50 | 20 | 20 | 10 | Excellent |
| 15 | 60 | 20 | 10 | 10 | Good |
| 16 | 30 | 20 | 40 | 10 | Good |
| 17 | 20 | 20 | 50 | 10 | Good |
| 18 | 60 | 10 | 20 | 10 | Poor-(little separation) |
| 19 | 40 | 30 | 20 | 10 | Poor- (very slow) |
| 20 | 40 | 40 | 10 | 10 | Poor- (very slow) |

TABLE 6

Optimum Separation Quality For Four-Component Media Occurs Using 10% PBF

| Run No. | Cellulose (%) | Glass (%) | Synthetic Staple (PET) (%) | Synthetic Binder (PBF) (%) | Separation Quality |
|---|---|---|---|---|---|
| 14 | 50 | 20 | 20 | 10 | Excellent (Fastest absorption) |
| 21 | 50 | 20 | 10 | 20 | Excellent (Slowest absorption) |
| 22 | 50 | 20 | 25 | 5 | Excellent (Medium absorption) |

Based on the foregoing results, it is concluded that experiment has shown that separation of erythrocytes from whole blood in four-component, single-layer, composite media of the present invention is effected when the following percentages by weight of the individual constituents are used: glass microfiber, 10–40%; cellulose, 20–60%; PET synthetic staple fiber, 10–50%; and PBF synthetic binder fiber, up to 20%. The individual percentages are such that the total percentage is 100%.

Optimum separation, as determined by uniformity of the separation, width of the separation zone, absorption time of the whole blood, and minimal hemolysis of erthrocytes, occurs when the percentages by weight of the individual constituents are: glass microfiber, 20%; cellulose, 50%; PET synthetic staple fiber, 20%; and PBF synthetic binder fiber, 10%. The percentage of glass microfibers again results in a bulk density of less than 0.1 g/cm$^3$ of glass microfiber material, typically about 0.05 g/cm$^3$.

Table 7 shows the results of a comparison of the tensile strength of a composite fibrous sheet formed according to the second preferred embodiment of the present invention with the tensile strength of a sheet of approximately equal thickness formed entirely from binderless glass microfiber. Tensile strength is defined as the force needed to pull apart a 2.5 cm width strip clamped between two jaws. The two sheets had approximately equal capillary transport mobility or rise, defined as the height to which distilled water will rise in a 2.5 cm width strip in one minute. Other parameters shown in Table 7 are: weight—the unit weight of a defined area of media; flow rate—the volume of water passing through a 5 cm diameter media sample in one minute at a constant 5 cm head of water; wet burst—the height of a column of water which will rupture a saturated 5 cm media sample; absorption time—the time needed for a pendant drop (approximately 50 μl) of citrated blood to completely absorb into the media surface; separation zone—the width of the clear plasma zone around a fully absorbed pendant drop of citrated bovine blood; and absorptive capacity—the amount of fluid, expressed in a weight percentage, in a saturated medium.

TABLE 7

Four-Component Composite Sheet Exhibits Greater Dry Tensile Strength Than Glass Microfiber Sheet

| Composition | Binderless glass microfiber | 4-component experimental composite |
|---|---|---|
| Weight (g/m$^2$) | 56 | 77 |
| Thickness (mm) | 0.30 | 0.33 |
| Capillary rise (mm/1 min) | 52 | 49 |
| Wet Burst (cm H$_2$O) | 19 | 18 |
| Dry Tensile Strength (lb/in) | | |
| machine direction | 2.1 | 3.6 |
| cross direction | 1.6 | 2.1 |
| Blood absorption time (sec) | 7.0 | 7.7 |
| Blood separation zone (mm) | 3.0 | 2.8 |
| Absorptive capacity (%) | | |
| H$_2$O | 727 | 449 |
| Bovine blood | 1037 | 633 |

The composite sheet had a dry tensile strength of 3.6 pounds per inch in the machine direction as compared to 2.1 pounds per inch for the glass microfiber sheet, a 71 percent increase, and 2.1 pounds per inch in the cross direction as compared to 1.6 pounds per inch, a 31 percent increase. The composite sheet exhibited lower absorptive capacity. Since the absorptive capacity of the composite sheet is less than that of the glass microfiber sheet, a smaller volume of blood will saturate the composite sheet. This is a distinct advantage in low volume applications, such as assay of fingerstick samples.

Materials other than synthetic binder fibers can be added to the composite to impart strength. These materials include acrylic latex, polyvinyl acetate, or other fibers. However, such materials can sometimes interfere with the chemical reactions in a particular assay and/or separation quality, and hence are not preferred.

Fibrous sheet formed according to the second preferred embodiment was tested with a range of standard suspensions of precision spherical particles having diameters comparable to the diameters of erythrocytes. When the resultant filtrates were analyzed using a Coulter TM particle counter, it was found that when the particles were 2.1–2.3 μm in diameter, approximately 98 percent of the particles were retained by the sheet. Since erythrocytes are typically 4–6 μm in size, separation efficiency should approach 100 percent.

We claim:

1. A composite medium for separating plasma or serum from whole blood, said composite comprising glass microfibers having a bulk density of less than 0.1 g/cm$^3$, cellulose fibers, and synthetic textile staple fibers, intermixed in a single layer.

2. The medium of claim 1, wherein the material constituting said glass microfibers is selected from the group consisting of alkali-containing borosilicate glass, alkali-free borosilicate glass, and pure quartz.

3. The medium of claim 2, wherein the mean diameter of said glass microfibers is in the range 0.3–0.7 μm.

4. The medium of claim 1, wherein the percentage by weight of said glass microfibers is in the range about 20–40 percent, the percentage by weight of said cellulose fibers is in the range about 20–50 percent, and the percentage by weight of said synthetic textile fibers is in the range about 20–60 percent.

5. The medium of claim 1, wherein the percentage by weight of said glass microfibers is about 20 percent, the percentage by weight of said cellulose fibers is about 35 percent, and the percentage by weight of said synthetic textile fibers is about 45 percent.

6. The medium of claim 1, wherein the mean bulk density of said composite is in the range about 0.20–0.30 g/cm$^3$.

7. The medium of claim 1, wherein the mean bulk density of said glass microfibers is about 0.05 g/cm$^3$.

8. The composite medium of claim 1, further including synthetic textile binder fibers having melting point temperature less than the melting point temperature of said synthetic textile staple fibers.

9. The medium of claim 8, wherein the material constituting said glass microfibers is selected from the group consisting of alkali-containing borosilicate glass, alkali-free borosilicate glass, and pure quartz.

10. The medium of claim 8, wherein the mean diameter of said glass microfibers is in the range 0.3–0.7 μm.

11. The medium of claim 8, wherein the percentage by weight of said glass microfibers is in the range about 10–40 percent, the percentage by weight of said cellulose fibers is in the range about 20–60 percent, the percentage by weight of said synthetic textile staple fibers is in the range about 10–50 percent, and the percentage by weight of said synthetic textile binder fibers is in the range 1–20 percent.

12. The medium of claim 8, wherein the percentage by weight of said glass microfibers is about 20 percent, the percentage by weight of said cellulose fibers is about 50 percent, the percentage by weight of said synthetic textile staple fibers is about 20 percent, and the percentage by weight of said synthetic textile binder fibers is about 10 percent.

13. The medium of claim 8, wherein the mean bulk density of said composite is in the range about 0.20–0.30 g/cm$^3$.

14. The medium of claim 8, wherein the mean bulk density of said glass microfibers is about 0.05 g/cm$^3$.

15. A process for separating plasma or serum from whole blood, comprising:
providing a single-layer, composite sheet comprising glass microfibers having a mean bulk density of less than 0.1 g/cm$^3$ and mean diameter in the range 0.3–0.7 μm, cellulose fibers, and synthetic textile staple fibers; and
slowly trickling whole blood onto one side of said sheet, whereby plasma or serum separated from the blood becomes available on the surface of said side and in the interior of said sheet.

16. A process as in claim 15, wherein said glass microfibers have a mean bulk density of about 0.05 g/cm$^3$.

17. A process as in claim 15, comprising:
providing a single-layer composite sheet further including synthetic textile binder fibers having melting point temperature lower than the melting point temperature of said synthetic textile staple fibers.

18. A process as in claim 17, wherein said glass microfibers have a mean bulk density of about 0.05 g/cm$^3$.

19. A single-layer, composite medium for separating plasma or serum from whole blood, having a mean bulk density in the range 0.20–0.30 g/cm$^3$, consisting of a mixture of:
glass microfibers having a mean diameter in the range 0.3–0.7 μm, a percentage by weight of about 20%, and a mean bulk density of about 0.05 g/cm$^3$;
cellulose fibers having a percentage by weight of about 35%; and
synthetic textile fibers having a percentage by weight of about 45%.

20. A single-layer composite medium for separating plasma or serum from whole blood, having a mean bulk density in the range 0.20–0.30 g/cm$^3$, consisting of a mixture of:
glass microfibers having a mean diameter in the range 0.3–0.7 μm, a percentage by weight of about 20%, and a mean bulk density of about 0.05 g/cm$^3$;
cellulose fibers having a percentage by weight of about 50%;
synthetic textile staple fibers having a percentage by weight of about 20%; and
synthetic textile binder fibers having a melting point temperature lower than the melting point temperature of said synthetic textile staple fibers, and a percentage by weight of about 10%.

* * * * *